United States Patent [19]

Gilbert

[11] 4,150,055
[45] Apr. 17, 1979

[54] REDUCTION AND DESULFONATION OF 2,4- AND 2,6-DINITROBENZENESULFONATES, WHICH MAY CONTAIN A METHYL GROUP IN THE 5-POSITION, TO PRIMARY AMINO COMPOUNDS

[75] Inventor: Everett E. Gilbert, Morristown, N.J.

[73] Assignee: The United States of America as represented by the Secretary of the Army, Washington, D.C.

[21] Appl. No.: 940,248

[22] Filed: Sep. 7, 1978

[51] Int. Cl.$^2$ .............................................. C07C 85/11
[52] U.S. Cl. .................................... 260/580; 260/582
[58] Field of Search ........................................ 260/580

[56] References Cited

U.S. PATENT DOCUMENTS 3,417,090  12/1968  Pelster et al. ...................... 260/288

OTHER PUBLICATIONS

Houben-Weyl, "Methoden Der Organischen Chemic," 4th Ed., vol. 10/1, Thieme Verlag, pp. 859-860, Stuttgart, (1971).
Groggins, "Unit Processes in Organic Synthesis," 5th Ed., pp. 358-362, (1958).
Kurz et al., "Biochemistry," vol. 16, (24), pp. 5207-5216, (1977).
Kurz et al., "J. Am. Chem. Soc.," vol. 97, (3), pp. 677-679, (1975).

Primary Examiner—Winston A. Douglas
Assistant Examiner—John Doll
Attorney, Agent, or Firm—Nathan Edelberg; Harold H. Card, Jr.; A. Victor Erkkila

[57] ABSTRACT

2,4- and 2,6- Dinitrobenzenesulfonates, which may contain a methyl group in the 5 position, are reduced with sulfur dioxide in aqueous sulfuric acid medium at elevated temperatures, whereby one or both nitro groups are reduced to a primary amino group and the sulfonic acid group is eliminated.

8 Claims, No Drawings

REDUCTION AND DESULFONATION OF 2,4- AND 2,6- DINITROBENZENESULFONATES, WHICH MAY CONTAIN A METHYL GROUP IN THE 5-POSITION, TO PRIMARY AMINO COMPOUNDS

GOVERNMENTAL INTEREST

The invention described herein may be manufactured, used, and licensed by or for the Government for governmental purposes without the payment to me of any royalties thereon.

BACKGROUND OF THE INVENTION

During the purification of crude TNT with aqueous sodium sulfite, a waste liquor is produced, which contains sodium 5-methyl-2,4- and -2,6-dinitrobenzenesulfonates, of which the major product is sodium 5-methyl-2,4-dinitrobenzenesulfonate. This waste liquor represents a disposal and pollution problem as well as a loss of the aforesaid sulfonates, which ordinarily amount to about 4% of the TNT produced.

SUMMARY AND DESCRIPTION OF THE INVENTION

An object of the present invention is to provide a novel process for recovering organic values from waste liquor containing 5-methyl-2,4- and -2,6-dinitrobenzenesulfonates produced in the purification of crude TNT with aqueous sulfite.

Another object of the invention is to provide a novel process for concurrently reducing and desulfonating a nitro compound selected from the group consisting of 2,4-dinitrobenzenesulfonate, 2,6-dinitrobenzenesulfonate, 5-methyl-2,4-dinitrobenzenesulfonate and 5-methyl-2,6-dinitrobenzenesulfonate, to produce the corresponding unsulfonated primary amino or nitroamino compound.

The objects well become apparent as the invention is further described.

It has been found that the foregoing objects can be achieved according to the process of the present invention, wherein a nitro compound selected from the group consisting of 2,4-dinitrobenzenesulfonate, 2,6-dinitrobenzenesulfonate, 5-methyl-2,4-dinitrobenzenesulfonate and 5-methyl-2,6-dinitrobenzenesulfonate is reduced with sulfur dioxide is aqueous sulfuric and medium at elevated temperatures, whereby one or both nitro groups are reduced to a primary amino group and the sulfonic acid group is eliminated to produce the corresponding primary amino compound. The process is considered to be unobvious in that it effects both reduction of a nitro group and desulfonation concurrently.

The process of the present invention comprises reacting the dinitrosulfonate compound in aqueous medium with sulfur dioxide at a temperature between about 100° C. and 250° C., and preferably between about 150° C. and 200° C. The reaction is unduly slow or incomplete at temperatures substantially below 100° C., while excessive amounts of undesired by products are formed by operating at reaction temperatures substantially above about 250° C. The reaction can be carried out by mixing the dinitrosulfonate compound with an aqueous solution of sulfur dioxide and heating the mixture to reaction temperature in a closed vessel. Also, sulfur dioxide gas can be pumped into a pressure vessel containing an aqueous solution or suspension of the dinitrosulfonate, preferably heated to a reaction temperature. The dinitrosulfonate compound can be present in the form of the free sulfonic acid or a water soluble salt thereof. A reaction period of 1 to 10 hours is usually sufficient to effect the reduction and desulfonation reactions.

The sulfur dioxide is preferably employed in an amount ranging about from 3 to 15 mols sulfur dioxide per mol of nitro group to be reduced to a primary amino group. It is believed that the sulfur dioxide, in reducing a nitro group to a primary amino group, is oxidized to sulfuric acid, which catalyzes the desulfonation reaction in situ. The presence in the reaction mixture of additional sulfuric acid, beyond that generated in situ by oxidation of the $SO_2$ to sulfuric acid, is not necessary although not precluded in the present process.

The process of the present invention can be applied to waste liquor containing 5-methyl-2,4- and 2,6-dinitrobenzenesulfonates obtained as a by-product in the purification of TNT with aqueous sodium sulfite. These sulfonates can be converted thereby into 2-amino-4-nitrotoluene and/or 2,4-toluenediamine, which are valuable intermediates for preparing polyurethane resins. Prior to treatment with the sulfur dioxide, the normally alkaline waste liquor is rendered neutral or slightly acid by addition of sulfuric acid. The present process is simple and economical, since sulfur dioxide is available at TNT plants, and no special catalysts or costly reagents are required. Further, the process can help to reduce the pollution problem during processing of the waste water and also provide a monetary credit for the TNT process.

The following examples illustrate specific embodiments of the method of carrying out the process of the present invention.

EXAMPLE 1

50 ml. of "Red Water", obtained in the purification of crude TNT with aqueous sodium sulfite and containing 2.5 g. of a mixture of sodium 5-methyl-2,4- and 2,6-dinitrobenzenesulfonates, and which was acidified to pH 3.7 with sulfuric acid, were cooled to 5°–10° C. in an ice bath and $SO_2$ gas was introduced at that temperature until the liquor was saturated. The solution was then sealed in a glass lined pressure vessel and heated with agitation at 180° C. for 3 hours. The reaction mixture was cooled to room temperature and separated from a black sludge (2.6 grams) by filtration. The filtrate was rendered alkaline with aqueous sodium hydroxide and then extracted with methylene chloride. Evaporation of the solvent from the extract yielded 0.3 g. of a reddish oil, which soon crystallized to a solid and was identified as 2-amino-4-nitrotoluene by its infrared spectrum. The aqueous solution separated from the methylene chloride extract was neutralized and evaporated to dryness and the residue was extracted with 100 ml. of isopropanol. Evaporation of the resulting solution to dryness yielded 1.2 g. of a solid, which was identified as 5-methyl-2,4- and 2,6-dinitrobenzenesulfonates by their IR spectra. Since the original red water contained 2.5 g. of the sulfonates, the yield of 2-amino-4-nitrotoluene was 43% of theory based on the 5-methyl-2,4- and 2,6-dinitrobenzenesulfonates reacted.

EXAMPLE 2

Example 1 was repeated except that the reaction mixture was heated in the sealed pressure vessel at 160°–5° C. for 6 hours. The yield of 2-amino-4-nitrotoluene thus obtained was 0.4 g.

EXAMPLE 3

1.7 g. of anhydrous sodium 5-methyl-2,4-dinitrobenzenesulfonate (mol. wt. 284) and 50 ml. of water containing 6% by weight of $SO_2$ were charged to a glass-lined Parr bomb, which was then sealed and heated to 180° C. for 3 hours. The bomb was then chilled in an ice bath and opened, and the contents were filtered. The filter cake was dried, yielding 0.4 g. of solid which was identified as 2-amino-4-nitrotoluene acid sulfate (m.w. 201). The filtrate was evaporated to about ⅓ volume, and rendered neutral with conc. $NH_4OH$. The resulting precipitate was separated by filtration and dried, yielding 0.6 g. of solid which was identified by its infrared spectrum as the ammonium salt of 5-methyl-2,4-dinitrobenzenesulfonic acid. The filtrate was evaporated to dryness yielding 1.8 g. of solid which was identified by its infrared spectrum as ammonium sulfate. Thus, 35% of the starting compound was recovered, 31% was converted to 2-amino-4-nitrotoluene and 34% was unaccounted for.

EXAMPLE 4

1.7 g. of sodium 5-methyl-2,6-dinitrobenzenesulfonate containing 2.5 mols of water of crystallization (m.w. 329) and 50 ml. of water containing 6% $SO_2$ were charged to a glass lined Parr bomb and the mixture was heated to 180° C. for 3 hours. The reaction mixture was cooled to about 0° C. and separated from some black sludge (0.1 g.) by filtration. The filtrate was made alkaline with aqueous sodium hydroxide (a precipitate was formed) and then extracted with methylene chloride. The extract was evaporated to dryness, yielding 0.1 g. of a solid which was identified by its infrared spectrum as 2-amino-4-nitrotoluene. The aqueous liquor was neutralized and evaporated to dryness. The residue was dissolved in 90% isopropanol, and the resulting solution was filtered to remove a small amount of insoluble matter, and evaporated to dryness, yielding 0.8 g. of solid which was identified by its infrared spectrum as the starting compound. The yield of 2-amino-4-nitrotoluene thus obtained corresponded to about 24% of theory based on the sulfonate reacted.

EXAMPLE 5

1.3 g. of anhydrous sodium 2,4-dinitrobenzenesulfonate (m.w. 270) and 50 ml. of water containing 6% $SO_2$ were charged to a stainless steel Parr bomb provided with a magnetic stirrer, and heated to 215° C. for 3 hours. The reaction mixture was cooled to about 0° C. and filtered from black sludge (0.2 g., m.p. above 300° C.). The quite acid filtrate was made alkaline with 10% aqueous NaOH and the resulting precipitate was separated by filtration. The filter cake was washed with hot water and dried, yielding 0.2 g. of a yellow crystalline product of m.p. 113°–115° C. identified as 3-nitroaniline, corresponding to 30% of theory yield.

EXAMPLE 6

500 ml. of "Red Water" of the type described in example 1, were charged to a stainless steel, agitated autoclave and heated to 180° C. Sulfur dioxide gas was pumped in until the pressure in the autoclave reached 150 psi., and the resulting reaction mixture was agitated at 180° C. for one hour. Additional sulfur dioxide was then admitted to restore the pressure to 150 psi and the reaction mixture was further heated at 180° C. for one hour. Thereafter, more sulfur dioxide was introduced until the pressure reached 150 psi, after which the contents were agitated at 180° C. for one hour. The reaction mixture thus obtained was cooled to room temperature and worked up as described in example 1. The yield of 2,4-toluenediamine thus obtained was 50% of theory.

The foregoing disclosure is merely illustrative of the principles of this invention and is not to be interpreted in a limiting sense. I wish it to be understood that I do not desire to be limited to the exact details shown and described, because obvious modifications will occur to a person skilled in the art.

What is claimed is:

1. A process for the reduction of an aromatic nitro compound selected from the group consisting of 2,4-dinitrobenzenesulfonate, 2,6-dinitrobenzenesulfonate, 5-methyl-2,4-dinitrobenzenesulfonate and 5-methyl-2,6-dinitrobenzenesulfonate, which consists essentially in reacting said compound with sulfur dioxide in an aqueous medium containing sulfuric acid, whereby at least one of the nitro groups is reduced to a primary amino group and the sulfonic acid group is eliminated concurrently.

2. The process according to claim 1, wherein the reaction is carried out at a temperature within the range about from 100° C. to 250° C.

3. The process according to claim 1, wherein the aromatic nitro compound is 5-methyl-2,4-dinitrobenzenesulfonate or 5-methyl-2,6-dinitrobenzenesulfonate or a mixture thereof.

4. The process according to claim 1, wherein the amount of sulfur dioxide is at least 3 moles per mole of the dinitro compound.

5. The process according to claim 3, wherein 2-amino-4-nitrotoluene is produced.

6. The process according to claim 3, wherein 2,4-toluenediamine is produced.

7. The process according to claims 3 or 4, wherein the nitro compound is a mixture of 5-methyl-2,4-dinitrobenzenesulfonate and 5-methyl-2,6-dinitrobenzenesulfonate contained in waste liquor obtained as a by-product in the purification of 2,4,6-trinitrotoluene with aqueous sodium sulfite.

8. The process according to claim 7, wherein the reaction is carried out at a temperature between about 150° C. and 200° C.

* * * * *